United States Patent
Macpherson et al.

(10) Patent No.: US 8,709,223 B2
(45) Date of Patent: Apr. 29, 2014

(54) NANOTUBE ELECTROCHEMISTRY

(75) Inventors: Julie Victoria Macpherson, Coventry (GB); Patrick Robert Unwin, Rugby (GB)

(73) Assignee: The University of Warwick (GB)

( * ) Notice: Subject to any disclaimer, the term of this patent is extended or adjusted under 35 U.S.C. 154(b) by 549 days.

(21) Appl. No.: 12/733,018

(22) PCT Filed: Aug. 1, 2008

(86) PCT No.: PCT/GB2008/002634
§ 371 (c)(1),
(2), (4) Date: Feb. 1, 2010

(87) PCT Pub. No.: WO2009/016389
PCT Pub. Date: Feb. 5, 2009

(65) Prior Publication Data
US 2010/0133119 A1  Jun. 3, 2010

(30) Foreign Application Priority Data
Aug. 2, 2007  (GB) .................................. 0715077.4

(51) Int. Cl.
*G01N 27/327* (2006.01)
*G01N 27/30* (2006.01)
*C01B 31/02* (2006.01)
*B82Y 15/00* (2011.01)

(52) U.S. Cl.
CPC ............ *G01N 27/308* (2013.01); *C01B 31/022* (2013.01); *C01B 31/0273* (2013.01); *B82Y 15/00* (2013.01); *Y10S 977/742* (2013.01); *Y10S 977/773* (2013.01); *Y10S 977/957* (2013.01)
USPC ................... 204/403.14; 205/777.5; 205/792; 977/742; 977/773; 977/957

(58) Field of Classification Search
CPC ............ G01N 27/308; G01N 27/3271; C01B 31/022; C01B 31/0273; B82B 3/0014; B82B 3/0066; B82Y 15/00; B81B 7/04; B81B 2201/0214; B81B 2207/056
USPC ............... 204/400, 403.01–403.15, 431, 280, 204/290.01, 290.15; 205/777.5, 789, 792, 205/794.5; 977/701, 712, 742–753, 977/920–922, 953, 957, 958
See application file for complete search history.

(56) References Cited

U.S. PATENT DOCUMENTS

| | | | |
|---|---|---|---|
| 6,918,284 | B2 | 7/2005 | Snow et al. |
| 2004/0043527 | A1 | 3/2004 | Bradley et al. |

FOREIGN PATENT DOCUMENTS

| | | |
|---|---|---|
| WO | WO 2004/059298 | 7/2004 |
| WO | WO 2005/104179 | 11/2005 |

OTHER PUBLICATIONS

Wilson, NR, et al. "Assessment of the Electrochemical Behavior of Two-Dimensional Networks of Single Walled Carbon Nanotubes" Supporting Information, Analtical Chemistry, Oct. 1, 2006.*

(Continued)

*Primary Examiner* — J. Christopher Ball
(74) *Attorney, Agent, or Firm* — Cantor Colburn LLP

(57) ABSTRACT

The invention relates to electrodes for electrochemical analysis comprising: —an insulating surface; —carbon nanotubes situated on the insulating surface at a density of at least 0.1 $\mu m_{CNT}\ \mu m^{-2}$; and —an electrically conducting material in electrical contact with the carbon nanotubes; wherein the carbon nanotubes cover an area of no more than about 5.0% of the insulating surface. Methods of making such electrodes and assay devices or kits with such electrodes, are also provided.

19 Claims, 6 Drawing Sheets

(56) References Cited

OTHER PUBLICATIONS

Figure 1:
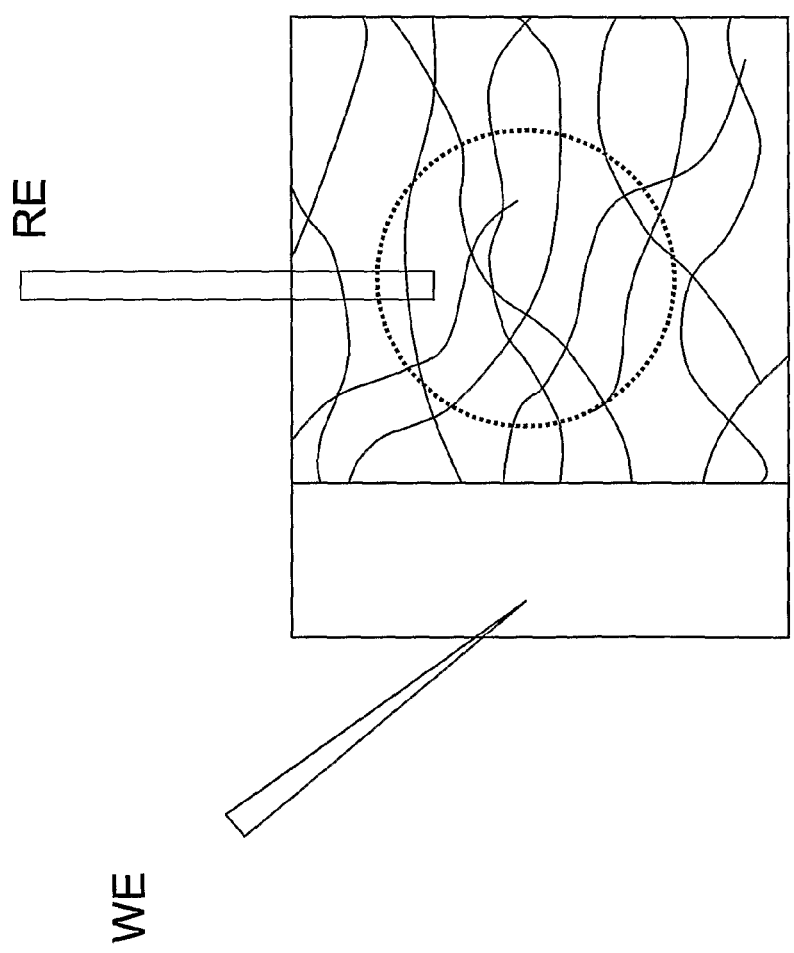

Neil R. Wilson et al., Assessment of the Electrochemical Behavior of Two-Dimensional Networks of Single-Walled Carbon Nanotubes, Anal. Chem., 2006, 78, pp. 7006-7015.

Tamir Gabay et al., Electro-chemical and biological properties of carbon nanotube based multi-electrode arrays, Nanotechnology, vol. 18, No. 3, pp. 6-29, Jan. 24, 2007.

John A. Rogers et al., High-performance electronics using dense, perfectly aligned arrays of single-walled carbon nanotubes, Nature, Apr. 4, 2007, vol. 2, p. 230.

Jonathan P. Edgeworth et al., Controlled growth and characterization of two-dimensional single-walled carbon-nanotube networks for electrical applications, Small, May 2007, vol. 3, No. 5, pp. 860-870.

Thomas M. Day et al., Electrochemical templating of metal nanoparticles and nanowires on single-walled carbon nanotube networks, J. Am. Chem. Soc., Aug. 2005, vol. 127, No. 30, pp. 10639-10647.

Thomas M. Day et al., Electrochemical and conductivity measurements of single-wall carbon nanotube network electrodes, J. Am Chem. Soc., Dec. 29, 2004, vol. 126, No. 51, pp. 16724-16725.

Thomas M. Day et al., Factors controlling the electrodeposition of metal nanoparticles on pristine single walled carbon nanotubes, Nano Lett., Jan. 2007, vol. 7, No. 1, pp. 51-57.

Ioana Dumitrescu et al., Functionalizing single-walled carbon nanotube networks: Effect on electrical and electrochemical properties, Journal of Physical Chemistry C 20070906, Am Chem. Soc. US, 2007 vol. 111, No. 35, pp. 12944-12953.

\* cited by examiner

NANOTUBE ELECTROCHEMISTRY

CROSS-REFERENCE TO RELATED APPLICATIONS

This application is a U.S. National Stage application of PCT/GB2008/002634 filed Aug. 1, 2008, which claims the benefit of GB 0715077.4 filed Aug. 2, 2007.

The present invention relates to an electrode comprising single-walled carbon nanotubes (SWNTs) or multi-walled nanotubes (MWNTs) for use in electrochemical, particularly amperometric, analysis and/or detection, and a method for the electrochemical analysis and/or detection of low concentration solutions using it.

Electrochemical and amperometric techniques have been used for some time in the analysis of the properties of compounds in solution. However, in order to obtain clear data measurements, a solution has to be at least of a certain concentration if any meaningful measurements are to be taken. If a solution of a compound to be analysed is too dilute, it is unlikely that the signal would be discernible from background readings.

One of the major limitations in the use of amperometric detection in electroanalysis is this discrimination against background and non-faradaic electrochemical processes, as they can seriously hamper low concentration detection measurements and trace level analysis. These background processes typically scale with the area of the electrode and can arise due to, for example, capacitative effects associated with charging of the surface, electrode surface reactions and solvent decomposition (at the limits of the potential window). One approach to tackling this problem has been the use of arrays of small area electrodes, arranged to minimize surface area whilst maximizing the current signals. Various configurations have been employed to date including for example, nanoporous filtration membranes filled with Au, or vertically aligned arrays of bundles of carbon nanotubes (50-100 nm domain size) insulated with epoxy resin or silicon oxide.

Carbon nanotubes are allotropes of carbon which exist in the form of long, narrow, hollow cylinders of graphite (called graphene). They may be several atoms in thickness (MWNTs) or just one-atom (SWNTs) thick, the latter having diameters of the order of about 1-3 nm. They can be formed in furnaces using carbon-containing gases or via vaporisation or arc discharge of/at a catalyst impregnated graphite block, and have been shown to exhibit electrical properties. They have been identified as potential electrode materials, since for SWNTs, typically, one out of every three SWNTs is a ballistic metallic conductor and the remaining proportion show semi-conducting properties. For MWNTs, it only needs one of the graphene cylinders to be metallic in nature for the MWNT to display metallic characteristics. Although it has been suggested that electron transfer may only occur at the ends of nanotubes or at defect sites, there is evidence that pristine (i.e. non-functionalised) carbon nanotubes show good characteristics as an electrode material. This is significant, as carbon is the electrode material of choice for bioelectrochemistry, with cyclic voltammetry (CV) being of particular importance for chemical identification in such systems. With macroscopic carbon electrodes, CV has typically been limited to a rather narrow concentration range, that being from about 10 µM-10 mM.

In the pristine state, the capacitance of a carbon nanotube is low. For most electrochemical studies on SWNTs and MWNTs, the nanotubes have been acid cleaned prior to use (a necessity due to the growth techniques employed), resulting in cut tubes with acid functionalised groups decorating the open ends and possibly also at defect sites along the tube length. The nanotubes are then either placed on a conducting support or potted in an insulator, back contacted and polished to expose the nanotubes. With both arrangements, acid treatment results in charged groups accumulating on the surface leading to increased capacitance. Non-faradaic and faradaic processes from the conducting support may also contribute to the signal. Additionally, double layer charging (capacitance) can be problematic if the insulating seal between the nanotube and the SWNT is leaky.

However, by growing the SWNTs or MWNTs directly, using e.g. catalysed chemical vapor deposition (cCVD), onto an insulating surface, it is possible to produce a pristine nanotube network. Importantly, using cCVD, acid cleaning of the sample is not necessary as the samples are very clean and therefore remain in a pristine state. The growth of SWNTs on insulating surfaces has been carried out previously, and such electrodes have been used in the electronics industry at both the single tube level and as two-dimensional networks and arrays.

At high enough densities, above the percolation threshold for metallic SWNTs, an SWNT two-dimensional network behaves as a thin metallic film, irrespective of the electrochemical formal potential of the redox couple. This can be achieved even at fractional surface coverages of the SWNTs as low as about 0.1%. Electrodes comprising SWNTs having densities and surface coverages of about 1% exist and have been characterised, and their electrochemical behaviour in mM level concentration surroundings has been investigated (Macpherson et al, *Anal. Chem.*, 2006, 78, 7006-7015). However, the potential of SWNT-network electrodes with metallic characteristics but low level surface coverage in the electrochemical detection and/or analysis of very low concentration solutions has never before been recognised. The same applies for SWNTs arranged in a two-dimensional array fashion or MWNTs in an array or network.

Other publications relating to the use of SWNT-comprising electrodes describe their use in e.g. gas sensors (U.S. Pat. No. 6,918,284, WO 2004/059298, WO 2005/104179), such as in mass spectrometry.

Other electrodes comprising carbon nanotubes also include a layer of another material situated between the nanotubes and a silicon dioxide substrate, such as passivated titanium nitride conductors (Gabay et al, Nanotechnology, Vol. 18, No. 3, pages 6-29, published 24 Jan. 2007).

US 2004/0043527 describes carbon nanotubes for detecting low concentrations of analytes, but is concerned with investigating the changes in the electrical properties of the nanotube network in response to an analyte, rather than direct electrochemical solution analysis, and is directed towards electrical (gate response and capacitative) applications.

However, none of the known research into SWNT-comprising electrodes includes a combination of low SWNT surface coverage with a density high enough to exhibit metallic behaviour, on the electrode surface. In each of the publications mentioned above, the electrodes used would not be suitable for the electrochemical analysis at very low concentration due to the level of background noise which would be created as a result of either (1) the high surface area coverage of the SWNTs; or (2) the increased capacitance arising from the non-pristine nature of the SWNTs. This also limits the electrodes to lower scan rates in cyclic voltammetry (CV) and an inability to access short times in potential step chronoamperometry. The background noise generated by such electrodes obscure the small signals derived from very low concentration solutions, thus rendering the electrodes unsuitable for such analysis.

It is therefore desirable to develop an electrode for electrochemical analysis which is capable of the analysis of (a) very low concentration solutions which are not measurable using macroscopic carbon electrodes (≥1 mm) or existing macro-sized SWNT-based electrodes, (b) faster scan CV and (c) shorter time analysis in potential step chronoamperometry, thus overcoming one or more of the problems described above.

The electrode of the invention comprises SWNTs (or MWNTs) in a two-dimensional network or array arrangement on an insulating surface, as an electrode material with unprecedented low background currents, which facilitates trace level (μM-nM or smaller) concentration CV measurements.

Therefore, in accordance with the present invention, there is provided an electrode for electrochemical analysis, comprising:
an insulating surface;
carbon nanotubes situated on the insulating surface at a density of at least 0.1 $\mu m_{CNT} \mu m^{-2}$; and
an electrically conducting material in electrical contact with the carbon nanotubes;
wherein the carbon nanotubes cover an area of no more than about 5% or no more than about 2%, preferably no more than about 0.8%, of the insulating surface. The area of the insulating surface covered by the carbon nanotubes may be that region of the electrode intended to be contacted with a sample for electrochemical analysis.

The carbon nanotubes may be either SWNTs or MWNTs, preferably SWNTs.

Electrodes having a surface coverage of no more than about 1% are capable of generating about 100-fold less background noise than conventional electrodes, enabling signals from trace level concentrations of analytes to be detected and analysed.

Preferably, the coverage of the carbon nanotubes on the insulating surface is no more than about 1.00, 0.75, 0.70, 0.65, 0.60, 0.55, 0.50, 0.45, 0.40, 0.35, 0.30, 0.25, 0.20, 0.15, 0.10, 0.05 or 0.01% of the insulating surface.

The density of the carbon nanotubes is preferably at least about 1 $\mu m_{CNT} \mu m^{-2}$ (i.e. about 1 μm of nanotube per μm² of surface), more preferably at least about 2, 3, 4, 5, 6, 7, 8, 9 or 10 $\mu m_{CNT} \mu m^{-2}$. For arrays of nanotubes, the density may be lower still, for example about 0.1 $\mu m_{CNT} \mu m^{-2}$.

For SWNTs, a density of carbon nanotubes of at least about 2.0 to about 3.0 $\mu m_{CNT} \mu m^{-2}$ is preferred.

Figure 2A:

The carbon nanotubes are preferably not localised over a small area of the electrode, but are distributed all over the electrode, though at low density, as illustrated in e.g. FIG. 2a.

The nanotubes are preferably oriented substantially parallel to the insulating surface. In the case of SWNT networks, each SWNT is preferably in contact with at least three other carbon nanotubes to maximise metallic conductance. This is because approximately one in every three SWNTs are metallic in nature, so this degree of interaction ensures that there is a consistent metal-metal contact across the network and hence conductance. More preferably, each SWNT is in contact with more than three others, such as 4, 5 or 6 others. However, on average, each SWNT is preferably in contact with at least three others. For carbon nanotube arrays, preferably no contacts are required as single tubes typically run parallel from a gold band.

The SWNTs may be in a network or array arrangement which is two-dimensional.

The dimensions of the SWNTs in a network are usually about 5-10 μm in length and about 1-3 nm in diameter. In an array growth, although the diameter of the SWNTs will be similar, they may be much longer, up to hundreds of micrometers in length.

In the networks the spacing between the carbon nanotubes on the electrode is dependent upon the density, which is controlled. The spacing is approximately 1/density (where density is measured as length of nanotube per unit area), for a minimum surface coverage of 0.1% (i.e. a density of 1 μm length of tube per μm²). This relates to a separation of about 10 μm. For arrays, the minimum surface coverage can be as low as 0.01%.

The insulating surface may be composed of any insulating material. According to one aspect of the invention, the surface may comprise silicon, particularly a silicon oxide, e.g. an $Si/SiO_2$ containing surface (i.e. silicon with a silicon oxide coating), or quartz. Alternatively, any insulating polymeric surface may be used. Most preferably, an $Si/SiO_2$ containing surface is used.

Electrical connection is preferably made at one end of the insulating surface using an evaporated band of an electrically conductive material, although more than one point of electrical contact may be provided at different points on the insulating surface, such as by more than one evaporated or sputtered band of an electrically conductive material. The electrically conducting material may be any material as long as it is sufficiently conducting. Any conducting material which can be evaporated or sputtered may be used. Preferred examples of the electrically conducting material include Au, Pt, Pd, Ag, Ti or Cr (or a combination thereof). Most preferably, Au is used. To ensure good contact, it is preferable to put an adhesive (sticking) layer down first such as Ti or Cr prior to putting the conducting layer down. In this configuration there is no need to insulate the nanotubes. At a sufficiently high density, and on typical voltammetric timescales, the network behaves predominantly like a thin metallic film even though the surface coverage is no more than about 1%, or 0.8%, i.e. a low surface area electrode. The sheet resistivity of such as film is <100 kΩ/square. To avoid problems such as ohmic drop contributing to the amperometric response small areas of the network are typically exposed to solution. This is most commonly achieved using photolithography; however, to avoid processing of the network a solution filled microcapillary electrochemical cell has also been employed. Importantly, for low concentration detection, the need to isolate only small areas of the network is no longer an issue as the current flowing will be small. In previous electrochemical studies with SWNT networks, small areas have been exposed to solution to minimize the effect of the network resistivity. Crucially, the low current density associated with low concentration detection, means that much larger network areas can be employed, thus simplifying the experimental arrangement significantly.

In one aspect of the invention, the nanotubes are pristine. In another aspect of the invention, the nanotubes are functionalised. If they are functionalised, they are preferably functionalised with functional groups and moieties selected from polymers (e.g. ion-exchange polymers, conducting polymers or redox polymers), oxido-reductase enzymes (e.g. glucose oxidase, cholesterol oxidase, nicotinamide adenine dinucleotide) and dopants (e.g. ferrocene), generally known in the art. Alternatively, the nanotubes may be partially coated by metal deposition. Preferred metals for deposition include metals such as Pt, Au, Ag, Cu, Hg, Pd and semi-conducting materials such as Ti, TiN, CdSe, CdTe or CdS, and organic polymers e.g. P3HT (poly-3-hexylthiophene), pentacene, doped polyaniline etc. Some of these materials can be further functionalised with self assembled monolayers and dopants.

According to a further aspect of the invention, it is also possible to functionalise the insulating surface on which the nanotubes are located, but leaving the nanotubes unfunctionalised. The functionalised surface could act to generate species which can be detected at the pristine nanotubes. The functionalisation would be carried out after the growth and addition of the electrically conducting material (e.g. Au). The methods for grafting functional groups on to e.g. silicon oxide surfaces is well known in the art.

Also provided within the scope of the invention is a method of manufacturing an electrode having a carbon nanotube array as described above thereon, comprising the steps of:
- depositing a quantity of catalytic nanoparticles onto an insulating surface;
- exposing the insulating surface to heat, a source of hydrogen gas, and a source of a carbon-containing gas to grow the nanotubes; and
- depositing an electrically conducting material on the insulating surface so that it is in electrical contact with the carbon nanotubes, wherein no annealing step is carried out prior to the deposition of the catalytic nanoparticles.

Omitting the annealing step enables better aligned growth to be obtained, minimising any tube-tube contacts in the nanotube arrays. For the arrays, it is desirable to have as little tube-tube contact as possible (preferably none), whereas for networks the degree of tube-tube contact is preferably high. Preferably, the deposition of the electrically conducting material is carried out after the growth of the nanotubes.

Methods for the preparation of carbon nanotube arrays have been developed by Rogers (J. A. Rogers et al., High Performance electronics using dense, perfectly aligned arrays of single-walled carbon nanotubes, Nature 2007, 2, 230).

Preferably, for efficient growth of carbon nanotube arrays, quartz is used as the substrate. Most preferably, patterned quartz (i.e. quartz patterned with a catalyst on the surface) is used. The carbon-containing gas is preferably $CH_4$.

The method developed for the preparation of carbon nanotube arrays in accordance with the present invention differs from that used by Rogers in that the quartz is not annealed prior to the deposition of the catalytic nanoparticles. Additionally, when an iron-based catalyst is used, the iron is provided in the form of ferritin, rather than from an e-beam of evaporated iron atoms (as ferritin is significantly cheaper and access to very sophisticated electron beam lithography is not required), as well as different oxidation and growth (reduction) conditions. The different oxidation and reduction conditions used in the Rogers method do not work with the ferritin catalyst and quartz substrates used in the invention.

According to one aspect of the invention, the carbon nanotubes are grown using chemical vapour deposition, such as catalysed chemical vapour deposition (cCVD). This allows for the direct growth of pristine nanotubes. The catalyst used is preferably iron- or cobalt-based, with iron-based catalysts being most preferred. One such source of iron is ferritin, an iron storage protein.

After the step of growing the nanotubes on an insulating surface, it is also possible to transfer the nanotubes from the original insulating surface to another insulating surface, such as a polymer surface.

According to a further aspect of the invention, the ultramicroelectrodes of any geometry, although discs are preferred, can be formed in accordance with the method detailed above if a layer of resist is then added and a confocal laser or mark aligner used to remove some of the resist in a defined area. For array formation it may also be necessary to lithographically pattern the Au contact electrode.

The present invention also provides a method of electrochemically analysing a solution using the electrode as described above wherein the solution has a concentration of no more than about 100 μM, preferably no more than about 10 μM, comprising:
(i) providing an insulating surface having carbon nanotubes situated thereon at a density of at least 0.1 $\mu m_{CNT} \mu m^{-2}$%, and an electrically conducting material in electrical contact with the carbon nanotubes, wherein the carbon nanotubes cover an area of no more than about 2.0% of the insulating surface;
(ii) bringing a sample of the solution into contact with the carbon nanotubes; and
(iii) applying a potential across the electrode to electrochemically analyse the sample.

The surface coverage of the nanotubes need only be 0.01% for nanotube arrays, but is preferably of the order of 0.1% for nanotube networks.

The method is preferably used in the electrochemical analysis of a solution having a concentration of no more than about 100 μM, or no more than about 10 μM, preferably no more than about 5 μM.

Preferably, the coverage of the carbon nanotubes on the insulating surface is no more than about 2.00, 1.00, 0.75, 0.70, 0.65, 0.60, 0.55, 0.50, 0.45, 0.40, 0.35, 0.30, 0.25, 0.20, 0.15, 0.10, 0.05 or 0.01% of the insulating surface. The density of the carbon nanotubes is preferably at least about 1 $\mu m_{CNT} \mu m^{-2}$, more preferably at least about 2, 3, 4, 5, 6, 7, 8, 9, 10 or 20 $\mu m_{CNT} \mu m^{-2}$. For arrays of nanotubes, the density may be lower still, for example about 0.1 $\mu m_{CNT} \mu m^{-2}$. Preferably the density is no more than about 20 $\mu m_{CNT} \mu m^{-2}$, more preferably no more than 10 $\mu m_{CNT} \mu m^2$.

The electrode and/or method of the invention can be used to electrochemically detect and analyse concentrations of about 2.5 μM or lower, 1 μM or lower, 100 nM or lower, 10 nM or lower, 1 nM or lower, or 100 pM or lower.

The solution to be analysed may have a concentration of an analyte on a nanomolar or picomolar scale, even down to femto- or attomolar levels, while still being able to be successfully electrochemically analysed using the electrode and the method of the invention.

When analysing a solution according to the invention, the solution is preferably brought into contact with the nanotubes by adding a droplet of it onto them. A potential is then applied between a working electrode in electrical contact with the electrically conducting material and a reference electrode (such as Ag/AgCl) which is positioned within the droplet. Droplets of the solution to be analysed are placed on the nanotubes on the insulating surface and create a relatively large planar diffusion area over the controlled density of nanotubes.

The electrode of the invention could also be extended to use in microelectrodes (i.e. (electrodes where the characteristic dimension is 100 μm or lower) and microelectrode arrays, using lithography to define the electrode area. Such microelectrodes (or ultramicroelectrodes—UMEs) present interesting attributes over conventional electrodes. Advantages include high mass transfer rates, short response times, low ohmic drop and reduced double layer charging. Traditionally, UMEs are made by sealing a fine wire in an insulator, by electrophoretic coating or using microlithographic techniques. Due to their useful properties, UMEs have found a wide range of applications in the fields of electroanalysis, sensors and scanning electrochemical microscopy.

The electrode of the invention could also be extended to flow systems and other detection methods, such as pulsed voltammetric methods and hydrodynamic modulation techniques, in addition to the droplet analysis. It can also serve as a platform on which modified layers could be added, such as polymers (e.g. ion exchange, redox), metal and semi-conducting nanoparticles. By moving to these new formats, the possibility for fast scan CV analysis and short time chronoamperometry is also realized.

The electrode of the invention is also envisaged as having application in biosensor technology. The nanotubes could be functionalised with e.g. enzymes such as glucose oxidase, cholesterol oxidase or nicotinamide adenine dinucleotide, including the use of polymers to aid the functionalisation and could be used in e.g. the analysis and/or detection of sugars such as glucose, or of other substances.

The electrode may be used in amperometric gas sensing, wherein the nanotube network electrode (pristine or functionalised as described herein) functions as a working electrode in a cell comprising an electrolyte (solution or polymer), designed in such a way to allow the ingress of an analyte gas, which is detected amperometrically.

The use of these electrodes (single or multiple) for in-vitro and in-vivo electrochemical measurements in biological tissues, relevant to chemical species such as neurotransmitters e.g. dopamine, serotonin, adrenaline in cellular and tissue environments is recognized. This includes measurements where the nanotube network electrode (pristine or functionalized) is held close to the region of interest and/or in direct contact with it.

The present invention therefore also envisages an assay device or kit which comprises an carbon nanotube-based electrode as described above. The assay device or kit may also further comprise a counter electrode, a reference electrode and optionally a flow cell, as well as preferably a recordal means for the obtaining of data. The reference electrode may be protected with a thin polymer film to enhance its stability.

The present invention will now be explained in more detail with reference to the accompanying Figures.

FIG. 1: This shows a schematic of an electrochemical set-up employing the SWNT network electrode as a detector of low concentration.

Figure 2B:
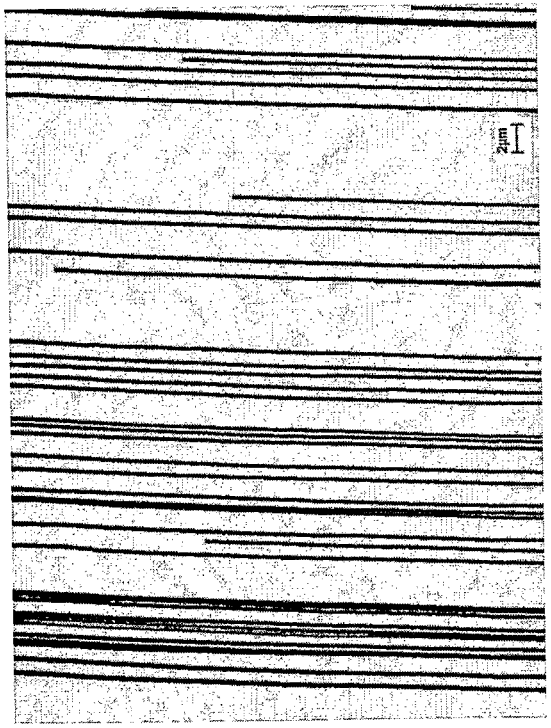

FIG. 2: This shows a field emission scanning electron microscopy (FE-SEM) image of (a) an SWNT network having a density of about 5 $\mu m_{SWNT} \mu m^{-2}$ (the scale bar represents 2 $\mu$m); and (b) a typical picture of an SWNT array on quartz.

Figure 3:
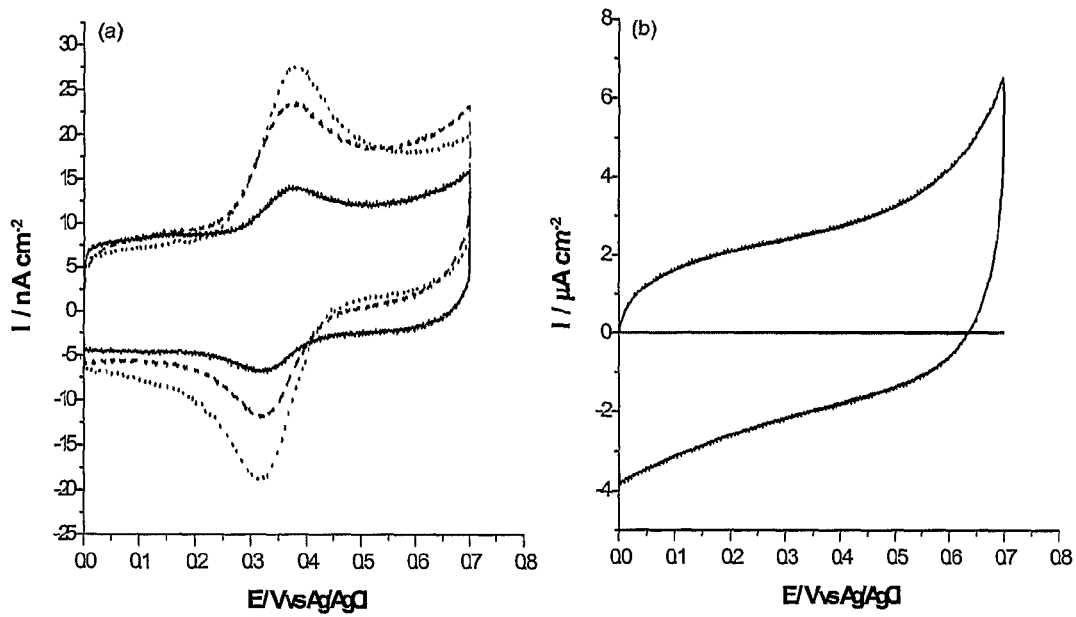

FIG. 3: This shows (a) CVs for the FcTMA$^{+/2+}$ couple (0.1 M NaCl) at concentrations of 25 nM (solid line), 70 nM (dashed line), and 100 nM (dotted line), recorded at a scan rate of 100 mV s$^{-1}$; (b) a CV showing the background response at a GCE in a 0.1 M NaCl solution, recorded at 100 mV s$^{-1}$. The red line shows the background response recorded at an SWNT network (0.1 M NaCl).

Figure 4:
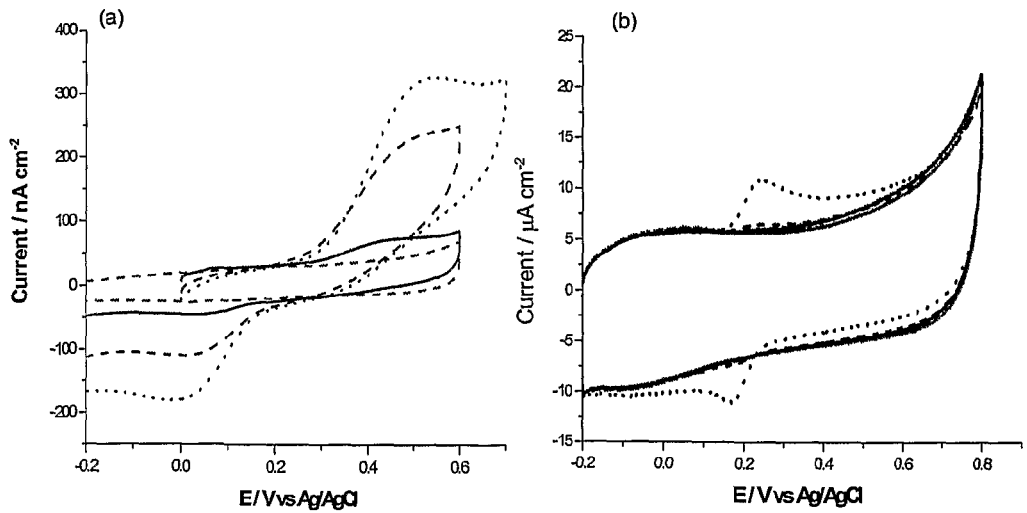

FIG. 4: This shows CVs for the oxidation of dopamine (in 0.1 M NaCl, 0.1 M acetic acid buffer, pH 5) at a scan rate of 100 mV s$^{-1}$: (a) an SWNT network electrode at concentrations of 100 nM (solid line), 500 nM (dashed line) and 1 $\mu$M (dotted line); (b) a GCE at concentrations of 100 nM (solid line), 1 $\mu$M (dashed line) and 10 $\mu$M (dotted line). In both cases the red line represents the background response without dopamine.

Figure 5:
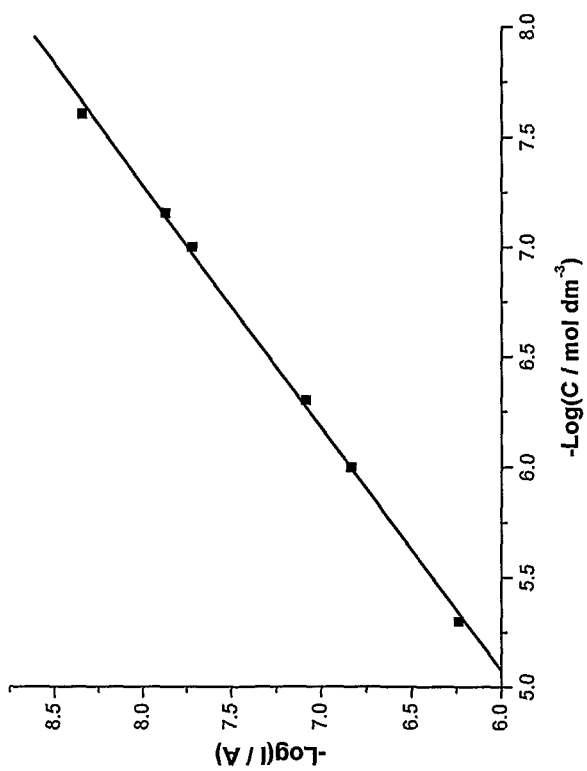

FIG. 5: This shows a plot of the logarithm of the anodic peak current versus the logarithm of FcTMA$^+$ concentration, for the oxidation of FcTMA$^+$ at varying concentrations in the range 25 nM-5 $\mu$M at an SWNT network electrode. The potential scan rate was 0.1 V s$^{-1}$ and NaCl served as the supporting electrolyte at a concentration of 0.1 M.

Figure 6:
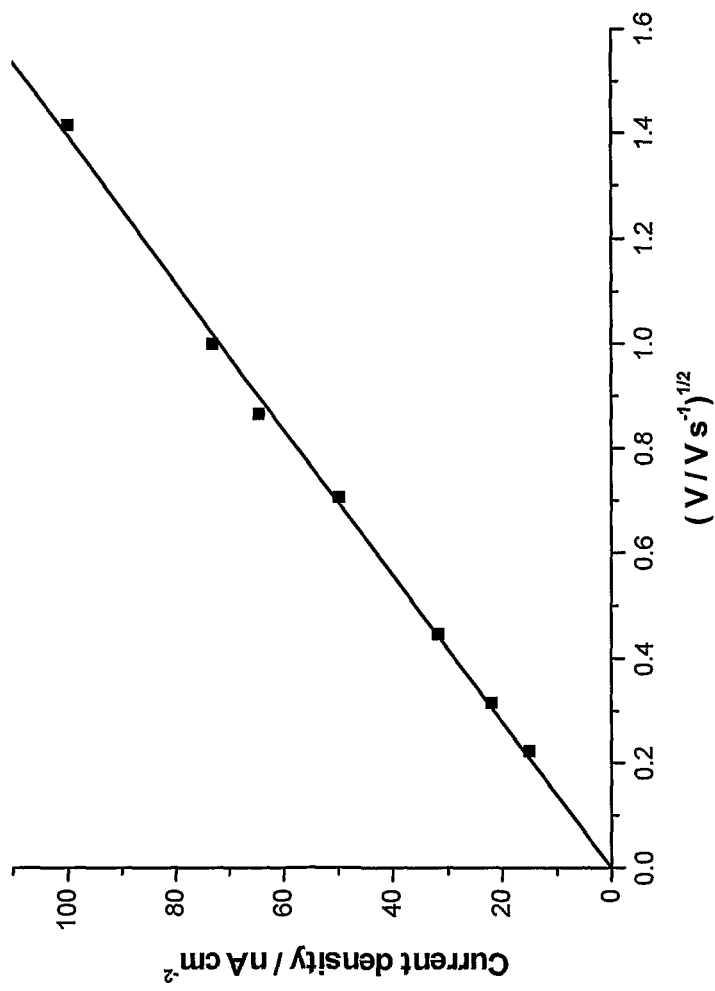

FIG. 6: Plot of the anodic peak current density versus square root of the scan rate for the oxidation of FcTMA$^+$ (100 nM) at an SWNT network electrode.

The invention will also be further explained in the following Examples, which are intended to be merely illustrative and are in no way intended to limit the scope of the invention.

Growth of SWNT networks by cCVD was carried out by placing highly doped Si substrates of about 1 cm square, with a 300 nm thermal oxide layer, in a 1 inch (2.54 cm) tube furnace, after deposition of Fe. Under a flow of $H_2$, the furnace was heated from room temperature to 700° C. in 10 minutes, and then from 700° C. to the growth temperature in a further 10 minutes. The furnace was held at this temperature for 5 minutes, and $CH_4$ was then introduced for a set period of time, this being the growth time. After growth, the substrate was allowed to cool in the furnace under a flow of $H_2$ only. Once the temperature had reached less than 200° C. the sample was removed. A complete growth cycle takes about 1 h, and up to 8 samples can be grown at any one time (limited by the temperature uniformity in the tube furnace used).

To control the positioning of the SWNTs in a network in particular regions on a substrate surface, this can be carried out either before or after SWNT growth, referred to as pre-growth patterning and post-growth patterning respectively. Pre-growth patterning involves restricting the SWNT network growth to certain areas by selective placement of the metal catalyst. This can be done using for example photolithography, electron beam lithography, 'soft' lithography or shadow masking.

Post-growth patterning involves selective removal of the SWNT network after growth by an etchant such as a $CO_2$ snow jet treatment, or an oxygen plasma treatment. Photolithography was used to pattern photoresist on a SWNT network sample, protecting the SWNT network except for in the desired regions. An oxygen plasma treatment (100 W for 1 minute at 6×10$^{-1}$ mbar in an Emitech K1050X Plasma Asher) was then used to remove the exposed SWNTs and the photoresist removed. The oxygen plasma completely removes the nanotubes that were exposed to the oxygen plasma, leaving sharply cut ends. The effective resolution of post-growth patterning is given by the average spacing between the nanotubes within the network; as a result it can easily be achieved to sub-micron accuracy and in any pattern that can be lithographically defined.

The ability to carry out CV measurements at low concentration using the electrode of the invention was assessed using the simple outer sphere redox species (ferrocenylmethyl)trimethylammonium, FcTMA$^+$, in a solution containing 0.1 M NaCl (purity>99.99%).

Materials:

(Ferrocenylmethyl)trimethylammonium hexafluorophosphate, (FcTMA$^+$PF$_6^-$), was obtained by metathesis of (ferrocenylmethyl)trimethylammonium iodide (FcTMA$^+$I$^-$, Strem Chemical Co.) following a procedure reported by Szentirmay and Martin, *Anal. Chem.* 1984, 56, 1898. NaCl (Trace Select™, purity≥99.99%), and dopamine hydrochloride were purchased from Sigma and used as received. Acetic acid/acetate buffer (0.1 M acetate) was prepared from sodium acetate and acetic acid. All aqueous solutions were prepared from Milli-Q reagent water (Millipore Corp.) with a resistivity≥18 MΩ cm at 25° C.

Cyclic voltammograms (CVs) were recorded using an electrochemical analyzer (CH Instruments, model CHI730A). A typical two electrode configuration was used, where the working electrode was an SWNT network contacted via a gold band and an Ag/AgCl wire (0.1 M NaCl) served as the reference electrode. When 10 $\mu$L of solution was placed on the SWNT network, the area of the working electrode was constant (about 0.125 cm$^2$) for all measurements during the timescale of a set of CV measurements.

FIG. 5 shows a plot of the logarithm of the anodic peak current versus the logarithm of the concentration of FcTMA$^+$ at an SWNT network for concentrations in the range 25 nM to 5 μM. In accordance with the Randles Sevcik equation (eq 1) which predicts the peak current, $i_p$, resulting from planar diffusion to an electrode of area, A (pertaining to a reversible redox process at 298K):

$$i_p = (2.69 \times 10^5) n^{3/2} AD^{1/2} Cv^{1/2} \quad (1)$$

where n is the number of electrons transferred per redox event, D and C are the diffusion coefficient and concentration of the redox species of interest and v is the potential scan rate, the peak current is linear with concentration in the range 25 nM to 5 μM.

The network electrode was electrically connected using a sharp prober placed on the Au electrically conducting band. SWNT networks with densities in the range 5±1 $\mu m_{SWNT}$ $\mu m^{-2}$ (defined as length of SWNT per $\mu m^2$) were employed for all experiments, corresponding to ca. 0.5±0.1% surface coverage. A drop of solution (10 μL; 4 mm diameter) containing the electroactive species of interest was placed on the network close to the Au band but avoiding contact. An Ag/AgCl (0.1 M NaCl) reference electrode was positioned within the drop to complete the circuit and CVs were recorded for different concentrations of FcTMA$^+$.

FIG. 3a shows typical CVs recorded at a potential sweep rate of 100 mV s$^{-1}$ for the FcTMA$^{+/2+}$ couple at concentrations of 25 nM (—), 70 nM (- - -), and 100 nM (···). Evidently, the response for a concentration of just 25 nM is easily discernible. It is important to note that although the network coverage is <1% of the surface, the current response is as if the entire surface was covered. This is due to overlap of the diffusion fields between adjacent nanotubes, causing the response to be controlled by planar diffusion. However, the low surface coverage means that the background current at the network electrode is more than two orders of magnitude smaller than would be expected for a planar electrode. This point is further demonstrated in FIG. 3b which shows the CV response for a solution containing 0.1 M NaCl at a conventional glassy carbon electrode (GCE) and a SWNT network electrode.

Given the diffusion coefficient for FcTMA$^+$ of $6 \times 10^{-6}$ cm$^2$ s$^{-1}$, the expected peak oxidation current density for a FcTMA$^+$ concentration of 100 nM at a uniform electrode is about 21 nA cm$^{-2}$ (in accordance with the Randles-Sevcik equation), in good agreement with the experimentally measured peak current. The peak current for the oxidation of FcTMA$^+$ was found to scale linearly with concentration over the range 25 nM-5 μM, as did the peak current with the square root of the scan rate for a particular redox mediator concentration. The peak-peak separations for the FcTMA$^+$ CVs shown in FIG. 3 are 77 mV (25 nM); 71 mV (70 nM) and 71 mV (100 nM), reasonably close to reversible for this one electron redox process. As the concentration was further increased the voltammetric waves became more distorted, increasing from about 90 mV (1 μM) to about 240 mV (10 μM). This is not unexpected and arises primarily from ohmic effects in the network, which become more pronounced as the current magnitude increases.

To examine the applicability of SWNT network electrodes for trace level measurements of more complex electrode processes, the CV response for the neurotransmitter dopamine was investigated, which is oxidized in a two electron process. Adsorption of dopamine is thought to be a key step in the mechanism.

FIG. 3a shows CVs recorded at a scan rate of 100 mV s$^{-1}$ for the oxidation of dopamine, which forms dopamine o-quinone on the forward step, at concentrations of 100 nM (solid black line), 500 nM (dashed line) and 1 μM (dotted line) in a solution containing 0.1 M NaCl and 0.1 M acetic acid (buffered to pH 5). For comparison, the CV response for 100 nM (solid black line), 1 μM (dashed line) and 10 μM (dotted line) dopamine at a GCE, in the same solution, is shown in FIG. 3b.

The GCE shows quasi-reversible electron transfer characteristics ($\Delta E_p \sim 80$ mV), but this is only evident at a concentration of 1 μM or greater. In contrast, although the CVs for dopamine electrolysis at the pristine SWNTs are electrochemically sluggish a concentration of 100 nM can easily be measured. The background currents, at a potential where dopamine is not oxidized, are slightly higher than for FcTMA$^+$ oxidation. However, they are significantly lower than previous reports for nanotube-modified electrodes, as a consequence of the significantly reduced surface area and the pristine nature of the SWNTs used herein. The small increase in background current may be due to adsorption of dopamine on the nanotube surface increasing capacitive charging effects during potential scans.

Nonetheless, these CVs show the highest detection sensitivity for dopamine at an untreated carbon-based electrode material and highlight the promising nature of native SWNTs in electroanalysis.

Calculating Network Densities and Related Parameters

The high contrast in an FE-SEM (field emission-scanning electron microscopy) image of a SWNT network enables the use of standard image analysis software (e.g. freeware WSxM) to accurately extract the length of nanotube per unit area by 'flooding analysis'. This can be done quickly, and over large areas of a sample resulting in an accurate determination of network density and of the variation in network density across a sample. The length per unit area will only include the SWNTs connected to the network, and where bundles of nanotubes are present will count only the length of the bundle not the lengths of the individual nanotubes within it. As a result this method will give an underestimate of the amount of nanotubes present, but will give a fair representation of the network density.

The average length of the SWNTs within the network can be estimated by dividing the total length of the nanotube network, L, by the number of ends visible in the FE-SEM image. More precisely L=nρ/number of ends per unit area (wherein ρ=SWNT density), where if only one end of the nanotube is present n=1, and if both are present n=2. Here an intermediate value of n=1.5 is used. This is an estimate and it is time consuming to count all of the nanotube ends, as a result it is neither practical nor relevant to do this for every FE-SEM image.

From the length of nanotube per unit area, along with knowledge of the average length and average diameter found from AFM, many other parameters can be estimated, for example;
(i) Number per unit area=length per unit area/average length
(ii) Fractional surface coverage=length per unit area*average diameter
(iii) 'film thickness'=fractional surface coverage*average diameter
(so that film thickness*area=volume of nanotubes)
The average separation between the nanotubes can also be estimated from the relation:
(iv) Length per unit area*average separation=1

The area closer to one nanotube than any other is on average equal to the average separation between nanotubes times their average length, from which it is also possible to roughly estimate:

(v) Average number of crossings per nanotube~average length/average separation

For typical average diameters of about 1 nm and lengths of about 10 μm, the following parameters for the given values of network density can be estimated:

| Density (μm μm-2) | Density (number μm-2) | Fractional Surface Coverage (%) | Average Separation (μm) | Crossings per Nanotube | 'Film thickness' (nm) |
|---|---|---|---|---|---|
| 0.1 | 0.01 | 0.01 | 10 | 1 | $10^{-4}$ |
| 1 | 0.1 | 0.1 | 1 | 10 | $10^{-3}$ |
| 10 | 1 | 1 | 0.1 | 100 | $10^{-2}$ |

Theoretical modeling of percolation of straight, uniform length, high aspect ratio, conducting sticks predicts that the percolation threshold, $\rho_{th}$, is given by:

$$\rho_{th} = 17.94/(\pi^* l)$$

Clearly the nanotubes are neither necessarily straight nor of uniform length, however this can be used to get an estimate of the percolation threshold. For an average length of about 10 μm this implies $\rho_{th}$ is about 0.5 $\mu m_{SWNT} \mu m-2$ (wherein $\rho_{th}^{met}$ is the metallic percolation threshold, i.e. where there is a continuous metal pathway of metallic tubes in contact with each other). Hence the 'low' density sample referred to according to its conductivity response should indeed be above the percolation threshold, but given $\rho_{th}^{met}$ is about 3 $\rho_{th}$, should be below the metallic threshold. The 'high' density samples should be well above both percolation thresholds.

For MWNTs, as the majority will be metallic, in a network arrangement, it is only required to get above $\rho_{th}$ therefore enabling slightly lower densities to be employed. This analysis does not apply for nanotube arrays as there are no tube-tube contacts.

Nanotube networks are effective for trace-level CV measurements, offering a simple and effective route to concentration levels which have proved inaccessible to other electrode materials. With non-covalent modification of the surface, efforts to minimize stray capacitance, the use of pulsed potential techniques and hydrodynamic methods, there is considerable scope for further increasing the detection sensitivity and selectivity of these network electrodes. Moreover, through the use of microelectrode formats (nanotube network or array), there is scope for increasing analysis times in fast scan CV techniques and accessing shorter timescales in potential step chronoamperometry.

The invention claimed is:

1. An electrode for electrochemical analysis, comprising:
an insulating surface;
carbon nanotubes situated on the insulating surface at a density of at least 0.1 $\mu m_{CNT} \mu m^{-2}$;
an electrically conducting material in electrical contact with the carbon nanotubes;
wherein the carbon nanotubes cover an area of no more than about 1.0% of the insulating surface; and
wherein the carbon nanotubes are functionalised by a group or moiety selected from polymers, oxido-reductase enzymes and dopants.

2. The electrode according to claim 1, wherein the carbon nanotubes cover no more than about 0.8% of the insulating surface.

3. The electrode according to claim 1, wherein the polymers are selected from the group consisting of ion-exchange polymers, conducting polymers, and redox polymers.

4. The electrode according to claim 1, wherein the carbon nanotubes are partially coated by deposition of a material.

5. The electrode according to claim 4, wherein the material is selected from platinum, silver, palladium, gold, copper, mercury, titanium, CdSe, CdTe, CdS, P3HT, pentacene, and doped polyaniline.

6. The electrode according to claim 1, wherein the oxidoreductase enzymes are selected from the group consisting of glucose oxidase, cholesterol oxidase, and nicotinamide adenine dinucleotide.

7. The electrode according to claim 1, wherein the dopant is ferrocene.

8. The electrode according to claim 1, wherein the carbon nanotubes are oriented substantially parallel to the insulating surface.

9. An assay device or kit comprising an electrode according to claim 1, a counter electrode and a reference electrode.

10. The assay device or kit of claim 9, further comprising a flow cell.

11. The assay device or kit of claim 9, further comprising a recordal means.

12. A method of electrochemically analysing a solution, comprising:
providing an electrode comprising an insulating surface, said insulating surface having carbon nanotubes situated thereon at a density of at least 0.1 $\mu m_{CNT} \mu m^{-2}$, and an electrically conducting material in electrical contact with the carbon nanotubes, wherein the carbon nanotubes cover an area of no more than about 1.0% of the insulating surface; and wherein the carbon nanotubes are functionalised by a group or moiety selected from polymers, oxido-reductase enzymes and dopants;
bringing a sample of the solution into contact with the carbon nanotubes; and
applying a potential across the electrode to electrochemically analyse the sample,
wherein the solution has an analyte concentration of no more than about 100 μM.

13. A method according to claim 12, wherein the solution has an analyte concentration of no more than about 10 μM.

14. The method according to claim 12, wherein the polymers are selected from the group consisting of ion-exchange polymers, conducting polymers, and redox polymers.

15. The method according to claim 12, wherein the carbon nanotubes are partially coated by deposition of a material.

16. The method according to claim 15 wherein the material is selected from platinum, silver, palladium, gold, copper, mercury, titanium, TiN, CdSe, CdTe, CdS, P3HT, pentacene, and doped polyaniline.

17. The method according to claim 12, wherein the oxidoreductase enzymes are selected from the group consisting of glucose oxidase, cholesterol oxidase, and nicotinamide adenine dinucleotide.

18. The method according to claim 12, wherein the dopant is ferrocene.

19. The method according to claim 12, wherein the carbon nanotubes are oriented substantially parallel to the insulating surface.

* * * * *